(12) United States Patent
Slazas et al.

(10) Patent No.: US 11,452,623 B2
(45) Date of Patent: Sep. 27, 2022

(54) BRAIDED STENT WITH EXPANSION RING AND METHOD OF DELIVERY

(71) Applicant: DEPUY SYNTHES PRODUCTS, INC., Raynham, MA (US)

(72) Inventors: Robert Slazas, Pinecrest, FL (US); Ramin Tehrani, Hialeah, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 446 days.

(21) Appl. No.: 16/441,999

(22) Filed: Jun. 14, 2019

(65) Prior Publication Data

US 2019/0290458 A1  Sep. 26, 2019

Related U.S. Application Data

(62) Division of application No. 13/802,114, filed on Mar. 13, 2013, now Pat. No. 10,561,509.

(51) Int. Cl.
*A61F 2/82* (2013.01)
*A61F 2/852* (2013.01)
*A61F 2/86* (2013.01)
*A61F 2/90* (2013.01)
(Continued)

(52) U.S. Cl.
CPC ............... *A61F 2/82* (2013.01); *A61F 2/852* (2013.01); *A61F 2/86* (2013.01); *A61F 2/90* (2013.01); *A61F 2/95* (2013.01); *A61F 2002/9528* (2013.01); *A61F 2002/9665* (2013.01)

(58) Field of Classification Search
CPC .... A61F 2/82; A61F 2/95; A61F 2/852; A61F 2/86; A61F 2/90; A61F 2002/9528; A61F 2002/9665
See application file for complete search history.

(56) References Cited

U.S. PATENT DOCUMENTS

| 4,332,278 A | 4/1982 | Lalikos |
| 4,610,688 A | 9/1986 | Silvestrini |
| 4,754,685 A | 7/1988 | Kite |

(Continued)

FOREIGN PATENT DOCUMENTS

| CN | 101234046 A | 8/2008 |
| CN | 101779992 A | 7/2010 |

(Continued)

OTHER PUBLICATIONS

Notification of Reasons for Refusal issued in corresponding Japanese Patent Application No. 2020-024204 dated Feb. 2, 2021 (only English translation submitted).

(Continued)

*Primary Examiner* — Ashley L Fishback
(74) *Attorney, Agent, or Firm* — Troutman Pepper Hamilton Sanders LLP (57) ABSTRACT

A self-expanding braided stent includes at least a distal radial expansion ring added to a distal end of the stent body to increase a radial expansion force of the self-expanding braided stent in deployment of the stent, and to facilitate advancement of the stent through a delivery sheath by a core advancement wire. A proximal radial expansion ring is optionally added to a proximal end of the stent body to allow the stent to be recaptured following partial deployment by retraction of the core advancement wire, prior to full deployment of a proximal portion of the stent body.

17 Claims, 5 Drawing Sheets

(51) Int. Cl.
*A61F 2/95* (2013.01)
*A61F 2/966* (2013.01)

(56) References Cited

U.S. PATENT DOCUMENTS

| | | | |
|---|---|---|---|
| 5,064,435 A | 11/1991 | Porter | |
| 5,275,622 A | 1/1994 | Lazarus et al. | |
| 5,282,824 A * | 2/1994 | Gianturco | A61F 2/07 606/191 |
| 5,330,500 A | 7/1994 | Song | |
| 5,382,259 A | 1/1995 | Phelps et al. | |
| 5,387,235 A | 2/1995 | Chuter | |
| 5,423,849 A | 6/1995 | Engelson | |
| 5,476,508 A | 12/1995 | Amstrup | |
| 5,522,881 A | 6/1996 | Lentz | |
| 5,549,662 A | 8/1996 | Fordenbacher | |
| 5,556,413 A | 9/1996 | Lam | |
| 5,601,593 A | 2/1997 | Freitag | |
| 5,609,627 A | 3/1997 | Goicoechea | |
| 5,662,622 A | 9/1997 | Gore | |
| 5,702,418 A | 12/1997 | Ravenscroft | |
| 5,725,549 A | 3/1998 | Lam | |
| 5,728,131 A | 3/1998 | Frantzen | |
| 5,755,772 A | 5/1998 | Evans et al. | |
| 5,769,887 A | 6/1998 | Brown | |
| 5,776,161 A | 7/1998 | Globerman | |
| 5,817,126 A | 10/1998 | Imran | |
| 5,849,037 A | 12/1998 | Frid | |
| 5,851,217 A | 12/1998 | Wolff | |
| 5,855,601 A | 1/1999 | Bessler | |
| 5,899,935 A | 5/1999 | Ding | |
| 5,916,235 A | 6/1999 | Guglielmi | |
| 5,916,264 A | 6/1999 | Von Oepen | |
| 5,961,546 A * | 10/1999 | Robinson | A61F 2/07 623/1.14 |
| 6,010,529 A | 1/2000 | Herweck | |
| 6,015,432 A | 1/2000 | Rakos | |
| 6,033,436 A | 3/2000 | Steinke | |
| 6,036,725 A | 3/2000 | Avellanet | |
| 6,051,020 A | 4/2000 | Goicoechea | |
| 6,099,559 A | 8/2000 | Nolting | |
| 6,110,198 A | 8/2000 | Fogarty | |
| 6,123,722 A | 9/2000 | Fogarty et al. | |
| 6,123,723 A | 9/2000 | Kónya et al. | |
| 6,152,956 A | 11/2000 | Pierce | |
| 6,161,399 A | 12/2000 | Jayaraman | |
| 6,165,213 A | 12/2000 | Goicoechea | |
| 6,168,621 B1 | 1/2001 | Vrba | |
| 6,176,875 B1 | 1/2001 | Lenker | |
| 6,264,683 B1 | 7/2001 | Stack et al. | |
| 6,280,465 B1 | 8/2001 | Cryer | |
| 6,319,278 B1 | 11/2001 | Quinn | |
| 6,325,823 B1 | 12/2001 | Horzewski | |
| 6,348,066 B1 | 2/2002 | Pinchuk et al. | |
| 6,391,037 B1 | 5/2002 | Greenhalgh | |
| 6,409,755 B1 | 6/2002 | Vrba | |
| 6,488,702 B1 | 12/2002 | Besselink | |
| 6,612,012 B2 | 9/2003 | Mitelberg et al. | |
| 6,626,936 B2 | 9/2003 | Stinson | |
| 6,635,080 B1 | 10/2003 | Lauterjung et al. | |
| 6,673,106 B2 | 1/2004 | Mitelberg et al. | |
| 6,699,277 B1 | 3/2004 | Freidberg et al. | |
| 6,740,113 B2 | 5/2004 | Vrba | |
| 6,673,107 B1 | 6/2004 | Brandt | |
| 6,770,089 B1 | 8/2004 | Hong et al. | |
| 6,818,013 B2 | 11/2004 | Mitelberg et al. | |
| 6,833,003 B2 | 12/2004 | Jones et al. | |
| 6,899,914 B2 | 5/2005 | Schmitz | |
| 6,911,040 B2 | 6/2005 | Johnson et al. | |
| 6,918,928 B2 | 7/2005 | Wolinsky | |
| 6,929,659 B2 | 8/2005 | Pinchuk | |
| 6,955,685 B2 | 8/2005 | Escamilla et al. | |
| 6,945,994 B2 | 9/2005 | Austin et al. | |
| 6,960,227 B2 | 11/2005 | Jones et al. | |
| 6,960,228 B2 | 11/2005 | Mitelberg et al. | |
| 6,970,734 B2 | 11/2005 | Eidenschink | |
| 7,001,422 B2 | 2/2006 | Escamilla et al. | |
| 7,037,331 B2 | 5/2006 | Mitelberg et al. | |
| 7,122,052 B2 | 10/2006 | Greenhaigh | |
| 7,153,324 B2 | 12/2006 | Case | |
| 7,201,769 B2 | 4/2007 | Jones et al. | |
| 7,208,008 B2 | 4/2007 | Clarke | |
| 7,267,685 B2 | 9/2007 | Butaric | |
| 7,288,111 B1 | 10/2007 | Holloway et al. | |
| 7,291,167 B2 | 11/2007 | DiCaprio | |
| 7,309,351 B2 | 12/2007 | Escamilla et al. | |
| 7,344,559 B2 | 3/2008 | Gray | |
| 7,462,190 B2 | 12/2008 | Lombardi | |
| 7,480,973 B2 | 1/2009 | Miller | |
| 7,628,806 B2 | 12/2009 | Yampolsky et al. | |
| 7,632,302 B2 | 12/2009 | Vreeman et al. | |
| 7,641,647 B2 | 1/2010 | Gunderson | |
| 7,655,031 B2 | 2/2010 | Tenne et al. | |
| 7,655,034 B2 | 2/2010 | Mitchell et al. | |
| 7,708,773 B2 | 5/2010 | Pinchuk et al. | |
| 7,758,629 B2 | 7/2010 | Holloway et al. | |
| 7,761,138 B2 | 7/2010 | Wang | |
| 7,806,919 B2 | 10/2010 | Bloom et al. | |
| 7,806,923 B2 | 10/2010 | Moloney | |
| RE42,244 E | 3/2011 | Boatman | |
| 7,913,371 B2 | 3/2011 | Klocke | |
| 7,985,213 B2 | 7/2011 | Parker | |
| 7,998,187 B2 | 8/2011 | Hartley et al. | |
| 8,021,418 B2 | 9/2011 | Gerberding | |
| 8,043,353 B2 | 10/2011 | Kaufmann et al. | |
| 8,043,357 B2 | 10/2011 | Hartley | |
| 8,048,139 B2 | 11/2011 | Frid et al. | |
| 8,052,741 B2 | 11/2011 | Bruszewski et al. | |
| 8,092,510 B2 | 1/2012 | Metcalf et al. | |
| 8,142,456 B2 | 3/2012 | Rosqueta | |
| 8,152,833 B2 | 4/2012 | Zaver | |
| 8,182,523 B2 | 5/2012 | Tenne et al. | |
| 8,187,316 B2 | 5/2012 | Kuppurathanam | |
| 8,357,194 B2 | 1/2013 | Majercak | |
| 8,372,133 B2 | 2/2013 | Douk et al. | |
| 8,394,119 B2 | 3/2013 | Zaver | |
| 8,449,600 B2 | 5/2013 | Hartley et al. | |
| 8,449,604 B2 | 5/2013 | Moaddeb | |
| 8,484,120 B2 | 7/2013 | Hagaman et al. | |
| 8,562,666 B2 | 10/2013 | Bonsignore | |
| 8,579,959 B2 | 11/2013 | Ducke | |
| 8,597,276 B2 | 12/2013 | Vongphakdy et al. | |
| 8,636,791 B1 | 1/2014 | Raju et al. | |
| 8,641,748 B2 | 2/2014 | Herbert et al. | |
| 8,672,992 B2 | 3/2014 | Orr | |
| 8,709,065 B2 | 4/2014 | Chobotov | |
| 8,734,501 B2 | 5/2014 | Hartley et al. | |
| 8,778,008 B2 | 7/2014 | Amplatz et al. | |
| 8,816,247 B1 | 8/2014 | Janardhan et al. | |
| 8,864,811 B2 | 10/2014 | Kao | |
| 9,078,731 B2 | 7/2015 | Mortarino | |
| 9,192,462 B2 | 11/2015 | Vinluan et al. | |
| 9,232,992 B2 | 1/2016 | Heidner | |
| 9,301,864 B2 | 4/2016 | Kao | |
| 9,320,590 B2 | 4/2016 | Zaver | |
| 9,339,260 B2 | 5/2016 | Eidenschink et al. | |
| 9,427,343 B2 | 8/2016 | Bogert | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |

(56) References Cited

U.S. PATENT DOCUMENTS

| | | |
|---|---|---|
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,713,523 B2 | 7/2017 | Zacharias |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,787,260 B2 | 10/2017 | Lehtola |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,004,513 B2 | 6/2018 | Leopold et al. |
| 10,058,421 B2 | 8/2018 | Eberhardt et al. |
| 10,076,428 B2 | 9/2018 | Gorochow |
| 10,143,551 B2 | 12/2018 | Braido et al. |
| 10,182,927 B2 | 1/2019 | Lorenzo |
| 10,206,796 B2 | 2/2019 | Tehrani et al. |
| 10,232,564 B2 | 5/2019 | Pelled |
| 10,292,851 B2 | 5/2019 | Gorochow |
| 10,321,991 B2 | 6/2019 | Glimsdale |
| 10,561,509 B2 | 2/2020 | Slazas et al. |
| 10,821,008 B2 | 11/2020 | Gorochow |
| 2001/0021873 A1 | 9/2001 | Stinson |
| 2001/0025195 A1 | 9/2001 | Shaolian |
| 2001/0049554 A1 | 12/2001 | Ruiz et al. |
| 2002/0095205 A1 | 7/2002 | Edwin |
| 2002/0111671 A1 | 8/2002 | Stenzel |
| 2002/0151953 A1 | 10/2002 | Chobotov |
| 2002/0151956 A1 | 10/2002 | Chobotov |
| 2002/0188344 A1 | 12/2002 | Bolea |
| 2002/0198587 A1 | 12/2002 | Greenberg et al. |
| 2003/0009211 A1 | 1/2003 | DiCarlo |
| 2003/0055493 A1 | 3/2003 | Carpenter |
| 2003/0114922 A1 | 6/2003 | Iwasaka |
| 2003/0144725 A1 | 7/2003 | Lombardi |
| 2003/0225448 A1 | 12/2003 | Gerberding |
| 2004/0015229 A1 | 1/2004 | Fulkerson |
| 2004/0024416 A1 | 2/2004 | Yodfat et al. |
| 2004/0044399 A1 | 3/2004 | Ventura |
| 2004/0073291 A1 | 4/2004 | Brown |
| 2004/0167619 A1 | 8/2004 | Case |
| 2004/0236406 A1 | 11/2004 | Gregorich |
| 2004/0254637 A1 | 12/2004 | Yang |
| 2005/0010281 A1 | 1/2005 | Yodfat et al. |
| 2005/0033406 A1 | 2/2005 | Barnhart |
| 2005/0043784 A1 | 2/2005 | Yampolsky et al. |
| 2005/0049668 A1 | 3/2005 | Jones et al. |
| 2005/0049669 A1 | 3/2005 | Jones et al. |
| 2005/0049670 A1 | 3/2005 | Jones |
| 2005/0125051 A1 | 6/2005 | Eidenschink |
| 2005/0131516 A1 | 6/2005 | Greenhalgh |
| 2005/0137682 A1 | 6/2005 | Justino |
| 2005/0148866 A1 | 7/2005 | Gunderson |
| 2005/0228484 A1 | 10/2005 | Stephens et al. |
| 2005/0234536 A1 | 10/2005 | Mitelberg |
| 2005/0257674 A1 | 11/2005 | Nishri et al. |
| 2005/0283220 A1 | 12/2005 | Gobran |
| 2005/0288775 A1 | 12/2005 | Dong |
| 2006/0015173 A1 | 1/2006 | Clifford |
| 2006/0064151 A1 | 3/2006 | Guterman |
| 2006/0064156 A1 | 3/2006 | Thistle |
| 2006/0069424 A1 | 3/2006 | Acosta |
| 2006/0195175 A1 | 8/2006 | Bregulla |
| 2006/0206202 A1 | 9/2006 | Bonhoeffer et al. |
| 2006/0212113 A1 | 9/2006 | Shaolian et al. |
| 2006/0271153 A1 | 11/2006 | Garcia |
| 2006/0271165 A1 | 11/2006 | Yip et al. |
| 2006/0287717 A1 | 12/2006 | Rowe |
| 2007/0005127 A1 | 1/2007 | Boekstegers |
| 2007/0043432 A1 | 2/2007 | Perouse |
| 2007/0060994 A1 | 3/2007 | Gobran |
| 2007/0100427 A1 | 5/2007 | Perouse |
| 2007/0156230 A1 | 7/2007 | Dugan |
| 2007/0167955 A1 | 7/2007 | Arnault De La Menardiere et al. |
| 2007/0191922 A1 | 8/2007 | Hartley |
| 2007/0203503 A1 | 8/2007 | Salahieh |
| 2007/0208373 A1 | 9/2007 | Zaver et al. |
| 2007/0208409 A1 | 9/2007 | Quigley |
| 2007/0213810 A1 | 9/2007 | Newhauser |
| 2007/0219612 A1 | 9/2007 | Andreas |
| 2007/0219613 A1 | 9/2007 | Kao |
| 2007/0233223 A1 | 10/2007 | Styrc |
| 2007/0233224 A1 | 10/2007 | Leynov |
| 2007/0233228 A1 | 10/2007 | Eberhardt et al. |
| 2007/0238979 A1 | 10/2007 | Huynh |
| 2007/0255385 A1 | 11/2007 | Tenne et al. |
| 2008/0009934 A1 | 1/2008 | Schneider et al. |
| 2008/0009938 A1 | 1/2008 | Huang |
| 2008/0071307 A1 | 3/2008 | DeBruyne et al. |
| 2008/0140172 A1 | 6/2008 | Carpenter |
| 2008/0221664 A1 | 9/2008 | Bales et al. |
| 2008/0221670 A1 | 9/2008 | Clerc |
| 2008/0243227 A1 | 10/2008 | Lorenzo |
| 2008/0281350 A1 | 11/2008 | Sepetka |
| 2008/0288046 A1 | 11/2008 | Hemerick |
| 2009/0005848 A1 | 1/2009 | Strauss |
| 2009/0030501 A1 | 1/2009 | Morris |
| 2009/0076594 A1 | 3/2009 | Sabaria |
| 2009/0082844 A1 | 3/2009 | Zacharias |
| 2009/0082845 A1 | 3/2009 | Chobotov |
| 2009/0082847 A1 | 3/2009 | Zacharias |
| 2009/0163951 A1 | 6/2009 | Simmons |
| 2009/0192588 A1 | 7/2009 | Shin |
| 2009/0198315 A1 | 8/2009 | Boudjemline |
| 2009/0234429 A1 | 9/2009 | Lau |
| 2009/0248133 A1 | 10/2009 | Bloom |
| 2009/0287145 A1 | 11/2009 | Cragg |
| 2009/0297582 A1 | 12/2009 | Meyer et al. |
| 2009/0306761 A1 | 12/2009 | Hebert et al. |
| 2009/0326640 A1 | 12/2009 | Yoshimura |
| 2010/0010619 A1 | 1/2010 | Tischler |
| 2010/0010622 A1 | 1/2010 | Lowe |
| 2010/0069948 A1 | 3/2010 | Veznedaroglu |
| 2010/0161028 A1 | 6/2010 | Chuter |
| 2010/0161036 A1 | 6/2010 | Pintor |
| 2010/0234935 A1 | 9/2010 | Bashiri |
| 2010/0249815 A1 | 9/2010 | Jantzen |
| 2010/0274282 A1 | 10/2010 | Olson |
| 2010/0292777 A1 | 11/2010 | Meyer |
| 2010/0298872 A1 | 11/2010 | Berndt |
| 2010/0324649 A1 | 12/2010 | Mattsson |
| 2010/0324651 A1 | 12/2010 | Holzer |
| 2010/0331972 A1 | 12/2010 | Pintor |
| 2011/0004237 A1 | 1/2011 | Schneider et al. |
| 2011/0060400 A1 | 3/2011 | Oepen |
| 2011/0137397 A1 | 6/2011 | Chan et al. |
| 2011/0184508 A2 | 7/2011 | Burmeister |

(56) References Cited

U.S. PATENT DOCUMENTS

| | | | |
|---|---|---|---|
| 2011/0264186 A1* | 10/2011 | Berglung | A61F 2/86 623/1.11 |
| 2011/0307049 A1 | 12/2011 | Kao | |
| 2012/0035714 A1 | 2/2012 | Ducke et al. | |
| 2012/0041538 A1 | 2/2012 | White | |
| 2012/0065728 A1 | 3/2012 | Galnor et al. | |
| 2012/0123529 A1 | 5/2012 | Levi | |
| 2012/0168022 A1 | 7/2012 | Rasmussen | |
| 2012/0191176 A1 | 7/2012 | Nagl | |
| 2012/0197377 A1 | 8/2012 | Ditter | |
| 2012/0271403 A1 | 10/2012 | Gries | |
| 2012/0283768 A1 | 11/2012 | Cox et al. | |
| 2012/0296418 A1 | 11/2012 | Bonyuet | |
| 2013/0041454 A1 | 2/2013 | Dobson | |
| 2013/0060323 A1 | 3/2013 | McHugo | |
| 2013/0123901 A1 | 5/2013 | Connor | |
| 2013/0144375 A1 | 6/2013 | Giasolli | |
| 2013/0245745 A1 | 9/2013 | Vong et al. | |
| 2013/0253572 A1 | 9/2013 | Molaei et al. | |
| 2013/0274849 A1 | 10/2013 | Zaver | |
| 2013/0345739 A1 | 12/2013 | Brady | |
| 2014/0025161 A1 | 1/2014 | Stankus et al. | |
| 2014/0135812 A1 | 5/2014 | Divino et al. | |
| 2014/0200607 A1 | 7/2014 | Sepetka et al. | |
| 2014/0200648 A1 | 7/2014 | Newell et al. | |
| 2014/0277332 A1 | 9/2014 | Slazas et al. | |
| 2014/0277360 A1 | 9/2014 | Girnary et al. | |
| 2014/0277376 A1 | 9/2014 | Lorenzo | |
| 2014/0277400 A1 | 9/2014 | Wainwright et al. | |
| 2014/0336741 A1 | 11/2014 | Connor | |
| 2015/0018458 A1 | 1/2015 | Ito | |
| 2015/0025625 A1 | 1/2015 | Rylski et al. | |
| 2015/0045831 A1 | 2/2015 | Allen | |
| 2015/0119974 A1 | 4/2015 | Rothstein | |
| 2015/0148882 A1 | 5/2015 | Ma et al. | |
| 2015/0265400 A1 | 9/2015 | Eidenschink | |
| 2015/0320556 A1 | 11/2015 | Levi | |
| 2015/0374483 A1 | 12/2015 | Janardham et al. | |
| 2016/0030155 A1 | 2/2016 | Cox et al. | |
| 2016/0038280 A1 | 2/2016 | Morriss | |
| 2016/0058524 A1 | 3/2016 | Ramin et al. | |
| 2016/0235561 A1 | 8/2016 | Wrobel et al. | |
| 2016/0302949 A1* | 10/2016 | Nishigishi | A61F 2/82 |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu et al. | |
| 2017/0027640 A1 | 2/2017 | Kunis et al. | |
| 2017/0027692 A1 | 2/2017 | Bonhoeffer et al. | |
| 2017/0027725 A1 | 2/2017 | Argentine | |
| 2017/0035436 A1 | 2/2017 | Morita | |
| 2017/0035567 A1 | 2/2017 | Duffy | |
| 2017/0042548 A1 | 2/2017 | Lam | |
| 2017/0049596 A1 | 2/2017 | Schabert | |
| 2017/0071737 A1 | 3/2017 | Kelley | |
| 2017/0072452 A1 | 3/2017 | Monetti et al. | |
| 2017/0079671 A1 | 3/2017 | Morero et al. | |
| 2017/0079680 A1 | 3/2017 | Bowman | |
| 2017/0079766 A1 | 3/2017 | Wang et al. | |
| 2017/0079767 A1 | 3/2017 | Leon-Yip | |
| 2017/0079812 A1 | 3/2017 | Lam et al. | |
| 2017/0079813 A1 | 3/2017 | Bar et al. | |
| 2017/0079817 A1 | 3/2017 | Sepetka et al. | |
| 2017/0079819 A1 | 3/2017 | Pung et al. | |
| 2017/0079820 A1 | 3/2017 | Lam et al. | |
| 2017/0086851 A1 | 3/2017 | Wallace et al. | |
| 2017/0086996 A1 | 3/2017 | Peterson et al. | |
| 2017/0095259 A1 | 4/2017 | Tompkins et al. | |
| 2017/0100126 A1 | 4/2017 | Bowman et al. | |
| 2017/0100141 A1 | 4/2017 | Morero et al. | |
| 2017/0100143 A1 | 4/2017 | Granfield | |
| 2017/0100183 A1 | 4/2017 | Iaizzo et al. | |
| 2017/0113023 A1 | 4/2017 | Steingisser et al. | |
| 2017/0147765 A1 | 5/2017 | Mehta | |
| 2017/0151032 A1 | 6/2017 | Loisel | |
| 2017/0156734 A1 | 6/2017 | Griffin | |
| 2017/0165062 A1 | 6/2017 | Rothstein | |
| 2017/0165065 A1 | 6/2017 | Rothstein et al. | |
| 2017/0165454 A1 | 6/2017 | Tuohy et al. | |
| 2017/0172581 A1 | 6/2017 | Bose et al. | |
| 2017/0172766 A1 | 6/2017 | Vong et al. | |
| 2017/0172772 A1 | 6/2017 | Khenansho | |
| 2017/0189033 A1 | 7/2017 | Sepetka et al. | |
| 2017/0189035 A1 | 7/2017 | Porter | |
| 2017/0196689 A1 | 7/2017 | Salahieh | |
| 2017/0215902 A1 | 8/2017 | Leynov et al. | |
| 2017/0216484 A1 | 8/2017 | Cruise et al. | |
| 2017/0224350 A1 | 8/2017 | Shimizu et al. | |
| 2017/0224355 A1 | 8/2017 | Bowman et al. | |
| 2017/0224467 A1 | 8/2017 | Piccagli et al. | |
| 2017/0224511 A1 | 8/2017 | Dwork et al. | |
| 2017/0224953 A1 | 8/2017 | Tran et al. | |
| 2017/0231749 A1 | 8/2017 | Perkins et al. | |
| 2017/0252064 A1 | 9/2017 | Staunton | |
| 2017/0265870 A1 | 9/2017 | Kealey et al. | |
| 2017/0265983 A1 | 9/2017 | Lam et al. | |
| 2017/0281192 A1 | 10/2017 | Tieu et al. | |
| 2017/0281331 A1 | 10/2017 | Perkins et al. | |
| 2017/0281344 A1 | 10/2017 | Costello | |
| 2017/0281375 A1 | 10/2017 | Longo | |
| 2017/0281909 A1 | 10/2017 | Northrop et al. | |
| 2017/0281912 A1 | 10/2017 | Melder et al. | |
| 2017/0290593 A1 | 10/2017 | Cruise et al. | |
| 2017/0290653 A1 | 10/2017 | Folan et al. | |
| 2017/0290654 A1 | 10/2017 | Sethna | |
| 2017/0290686 A1 | 10/2017 | Sirhan | |
| 2017/0296324 A1 | 10/2017 | Argentine | |
| 2017/0296325 A1 | 10/2017 | Marrocco et al. | |
| 2017/0303939 A1 | 10/2017 | Greenhalgh et al. | |
| 2017/0303942 A1 | 10/2017 | Greenhalgh et al. | |
| 2017/0303947 A1 | 10/2017 | Greenhalgh et al. | |
| 2017/0303948 A1 | 10/2017 | Wallace et al. | |
| 2017/0304041 A1 | 10/2017 | Argentine | |
| 2017/0304097 A1 | 10/2017 | Corwin et al. | |
| 2017/0304595 A1 | 10/2017 | Nagasrinivasa et al. | |
| 2017/0312109 A1 | 11/2017 | Le | |
| 2017/0312484 A1 | 11/2017 | Shipley et al. | |
| 2017/0316561 A1 | 11/2017 | Helm et al. | |
| 2017/0319826 A1 | 11/2017 | Bowman et al. | |
| 2017/0333228 A1 | 11/2017 | Orth et al. | |
| 2017/0333236 A1 | 11/2017 | Greenan | |
| 2017/0333678 A1 | 11/2017 | Bowman et al. | |
| 2017/0340383 A1 | 11/2017 | Bloom et al. | |
| 2017/0348014 A1 | 12/2017 | Wallace et al. | |
| 2017/0348514 A1 | 12/2017 | Guyon et al. | |
| 2018/0092766 A1 | 4/2018 | Gorochow | |
| 2018/0125649 A1 | 5/2018 | Nasr | |
| 2018/0263794 A1 | 9/2018 | Slazas et al. | |
| 2018/0333281 A1 | 11/2018 | Tehrani et al. | |
| 2019/0015229 A1 | 1/2019 | Fukutaki | |
| 2019/0021888 A1 | 1/2019 | Tehrani | |
| 2019/0038404 A1 | 2/2019 | Iamberger | |
| 2019/0038405 A1 | 2/2019 | Iamberger | |
| 2019/0053895 A1 | 2/2019 | Levi | |
| 2019/0053899 A1 | 2/2019 | Levi | |
| 2019/0224008 A1 | 7/2019 | Bressloff | |

FOREIGN PATENT DOCUMENTS

| | | |
|---|---|---|
| CN | 102100587 A | 6/2011 |
| CN | 102271620 A | 12/2011 |
| CN | 103330605 A | 10/2013 |
| CN | 103347466 A | 10/2013 |
| CN | 104042376 A | 9/2014 |
| CN | 104042380 A | 9/2014 |
| CN | 104582643 A | 4/2015 |
| CN | 105592826 A | 5/2016 |
| CN | 105832452 A | 8/2016 |
| DE | 202008014828 U1 | 2/2009 |
| DE | 102011015995 A1 | 10/2012 |
| DE | 10 2014 113836 A1 | 3/2016 |
| EP | 0701800 A1 | 3/1996 |
| EP | 0894505 A2 | 2/1999 |
| EP | 1488763 A2 | 12/2004 |

(56) References Cited

FOREIGN PATENT DOCUMENTS

| | | |
|---|---|---|
| EP | 1634546 A1 | 3/2006 |
| EP | 2545887 A1 | 1/2013 |
| EP | 2 777 642 A1 | 9/2014 |
| EP | 2777638 A1 | 9/2014 |
| EP | 2777649 A1 | 9/2014 |
| EP | 2915509 A1 | 9/2015 |
| EP | 3 311 782 A1 | 4/2018 |
| FR | 2939637 A1 | 6/2010 |
| JP | 11-57010 A | 3/1999 |
| JP | 11-57020 A | 3/1999 |
| JP | 3-503246 B2 | 3/2004 |
| JP | 2004-267750 A | 9/2004 |
| JP | 2013-541358 A1 | 11/2013 |
| JP | 2016-202248 A | 12/2016 |
| WO | 1989008433 A1 | 9/1989 |
| WO | WO 95/05132 A1 | 2/1995 |
| WO | 9943379 A1 | 9/1999 |
| WO | 2001/015632 A1 | 3/2001 |
| WO | 01/35864 A1 | 5/2001 |
| WO | 2001/058384 A1 | 8/2001 |
| WO | 2001/072240 A1 | 10/2001 |
| WO | 2005/087138 A1 | 9/2005 |
| WO | 2008/130530 A1 | 10/2008 |
| WO | 2012/082440 A1 | 6/2012 |
| WO | 2012/096687 A1 | 7/2012 |
| WO | 2013126299 A1 | 8/2013 |
| WO | 2013/151793 A1 | 10/2013 |

OTHER PUBLICATIONS

Examination report No. 1 for standard patent application issued in corresponding Australian Patent Application No. 2014201193 dated Oct. 13, 2017.

European Application No. 14159541.3 Search Report dated Aug. 4, 2014. Cited in parent application.

Extended European Search Report issued in corresponding European Patent Application No. 19 21 9438 dated Apr. 7, 2020.

Ansaar T. Rai et al., "Cerebrovascular geometry in the anterior circulation: an analysis of diameter, length and the vessel taper", J NeuroIntervent Surg 2013; 5: 371-375_ doi: 10_ 1136/neurintsurg-2012-010314; Apr. 4, 2012.

mig-welding.co.uk; Excerpt from with comment of Jun. 29, 2011 on pictures of welds.

mitcale.com; Welded connections excerpt, downloaded Dec. 6, 2012.

Navigate Tough Anatomy; brochure Copyright 2009; Codman & Shurtleff, Inc., 325 Paramount Drive, Raynham, Massachusetts.

Plug Weld Joining Two Plates; Excerpt from esabna.com, downloaded Dec. 6, 2012.

\* cited by examiner

BRAIDED STENT WITH EXPANSION RING AND METHOD OF DELIVERY

CROSS-REFERENCE TO RELATED APPLICATION

This application is a divisional application that claims priority to U.S. patent application Ser. No. 13/802,114 entitled "Braided stent with expansion ring and method of delivery" and filed Mar. 13, 2013, the contents of which are incorporated herein by reference in their entirety as if set forth verbatim.

BACKGROUND OF THE INVENTION

This invention relates generally to devices for interventional therapeutic treatment or vascular surgery for treatment of defects in the vasculature, and more particularly concerns a system and method for delivering a self-expanding braided stent to a treatment site in a vasculature of a patient.

Stents, which are tubular reinforcements inserted into a blood vessel to provide an open path within the blood vessel, have been widely used in intravascular angioplasty treatment of occluded cardiac arteries. In such applications, the stent is inserted after an angioplasty procedure or the like in order to prevent restenosis of the artery. In these applications, the stents are often deployed by use of inflatable balloons, or mechanical devices which force the stent open, thereby reinforcing the artery wall and provide a clear through-path in the center of the artery after the angioplasty procedure to prevent restenosis.

While such procedures may be useful in certain aspects of vascular surgery in which vasoocclusive devices are used, the weakness and tortuosity of the neurovasculature places limits on the applicability of such stents in procedures to repair neurovascular defects. Furthermore, the use of placement techniques, such as balloons or mechanical expansions of the type often found to be useful in cardiac surgery, are relatively less useful in vasoocclusive surgery, particularly when tiny vessels, such as those found in the brain, are to be treated. Hence, those skilled in the art have recognized a need for a stent compatible with techniques in vasoocclusive treatment of neurovascular defects that provides selective reinforcement in the vicinity of a neurovascular defect, while avoiding any unnecessary trauma or risk of rupture to the blood vessel.

Braided stents, typically formed from a plurality of elongate members, such as two or more metal wires, or polymeric fibers or strands of material, for example, can be very useful in treatment of neurovascular defects. However, one of the problems in deploying a self-expanding braided stent in a body lumen is activation of the initially expanding end, typically the distal end of the braided stent, to fully open. It is important that the initially expanding end should open fully, easily, and quickly, so that the rest of the length of self-expanding braided stent can be deployed, using the initially expanding end as an anchor point.

Stents made of braided wire also commonly have a high internal friction that resists the inherent radial expansion force of the self-expanding braided stent to open, particularly resisting opening of the initially expanding end, which can cause problems in anchoring and deployment of such self-expanding braided stents. Another common problem with deployment of braided stents is difficulty in advancing the compressed or crimped braided stent through a delivery sheath or microcatheter, typically also due to friction between the braided stent and the delivery sheath or microcatheter. Traditional delivery systems for braided stents push the braided stent in a distal direction by advancing a blunt surface against a proximal end of the braided stent, and consequently the application of force on the proximal end of the braided stent tends to axially compress the braided stent, causing the braided stent to expand radially. As a result, as the braided stent expands within the delivery sheath or microcatheter, an increased normal force is applied to the inner surface of the delivery sheath or microcatheter, increasing friction between the braided stent and the delivery sheath or microcatheter.

Current self-expanding braided stents typically depend solely on their material, dimension, cell design, and internal friction to expand. Deployment of such self-expanding braided stents commonly requires extra manipulation by a user to fully open the self-expanding braided stents, which affects placement accuracy and adds risk to the procedure. Proper deployment and fixation of the initial deployment end or distal end of a self-expanding braided stent are necessary for the subsequent proper alignment and positioning of the remainder of the stent body.

Another problem with deployment of self-expanding braided stents involves difficulty in recapturing a self-expanding braided stent after partial deployment and prior to full deployment of the stent. Currently, a self-expanding braided stent typically is advanced through a delivery sheath or microcatheter until the self-expanding braided stent emerges. When the self-expanding braided stent is unrestrained outside of the sheath or microcatheter, the self-expanding braided stent typically then expands and is deployed in the vasculature, making recapturing of the self-expanding braided stent difficult. self-expanding braided stent with increased radial expansion force, particularly at the initial deployment end or distal end, that can also reduce the internal friction of the braided stent during delivery of the braided stent through a delivery sheath or microcatheter, for improved ease and reliability of deployment of the self-expanding braided stent, particularly at the initial deployment end or distal end of the self-expanding braided stent.

It also would be desirable to provide an improved self-expanding braided stent that can be recaptured following partial deployment of a distal portion of the self-expanding braided stent prior to full deployment of a later deployed portion or proximal portion of the self-expanding braided stent. The present invention meets these and other needs.

SUMMARY OF THE INVENTION

Briefly and in general terms, the present invention provides for an improved self-expanding braided stent with one or more expansion rings, and methods of delivering the self-expanding braided stent through a delivery sheath or microcatheter to a treatment site in a patient's vasculature. The present invention provides for the addition of at least one radial expansion ring to an initial deployment end or distal end of a self-expanding braided stent to increase a radial expansion force of the self-expanding braided stent, for improved ease and reliability of deployment of the self-expanding braided stent, and particularly more reliable expansion and fixing of the initial deployment end or distal end of the self-expanding braided stent in deployment of the self-expanding braided stent. The addition of a radial expansion ring to a later deployed end or proximal end of a self-expanding braided stent allows the self-expanding braided stent to be recaptured following partial deployment of a distal portion of the self-expanding braided stent, and prior to full deployment of a later deployed portion or proximal portion of the self-expanding braided stent.

Accordingly, in a first embodiment, the present invention provides for a braided stent, including a tubular braided stent body formed from a plurality of elongate members, and one or more expansion rings disposed within and fixedly connected to at least one of the proximal end and the distal end of the tubular braided stent body. In a presently preferred aspect, the one or more expansion rings have a compressed configuration having a first diameter and an expanded configuration having a second diameter larger than the first diameter. In another presently preferred aspect, the plurality of elongate members may be formed by a plurality of metal wires, a plurality of polymeric fibers, a plurality of strands of material, or the like. In another presently preferred aspect, the braided stent is a self-expanding stent having a compressed configuration having an unexpanded diameter and an expanded configuration having an expanded diameter larger than the first diameter.

In another presently preferred aspect, the one or more expansion rings include a plurality of elongated connecting arm members having first ends at the first end of the one or more expansion rings and second ends at the second end of the expansion ring, and the plurality of elongated connecting arm members are connected sequentially to adjacent ones of the plurality of elongated connecting arm members alternatingly at the first and second ends to form a plurality of alternating elbow connections at the first and second ends, such as in a zigzag configuration, for example. In another presently preferred aspect, the one or more expansion rings are formed of shape memory material, such as a nickel titanium alloy or a shape memory polymer, for example, having a shape memory position in the expanded configuration. Preferably the one or more expansion rings is heat treated so that the shape memory position is an expanded zigzag type ring, and the plurality of elongated connecting arm members and the alternating elbow connections preferably are configured to be compressed into a small tubular shape during delivery. In another presently preferred aspect, the one or more expansion rings include a plurality of attachment tabs connected to the plurality of alternating elbow connections at the first ends of the one or more expansion rings, and preferably the plurality of alternating elbow connections at the first ends of the one or more expansion rings have exterior ends directed away from the plurality of elongated connecting arm members, and the plurality of attachment tabs are connected to the exterior ends of the plurality of alternating elbow connections at the first ends of the one or more expansion rings. The plurality of attachment tabs preferably are fixedly attached to the tubular braided stent body, such as by welding, soldering or gluing the attachment tabs to an expansion ring, for example. Alternatively, the attachment tabs can include holes in them so that a wire loop can be threaded through the attachment tabs, as well as through interstices of the braided stent to connect the attachment tabs and the braided stent together. In addition, two or more attachment tabs can be included at the ends of each elbow of the expansion ring, and the attachment tabs can then be used to capture a portion of the braided stent between them, after which the two or more attachment tabs can be secured together to be permanently secured to the braided stent by welding, soldering, adhesive, or the like. In another presently preferred aspect, an expansion ring is disposed within and fixedly connected to the initial deployment end or distal end of the tubular braided stent body, and a proximal expansion ring optionally also may be disposed within and fixedly connected to the later deployed end or proximal end of the tubular braided stent body.

In another presently preferred aspect, a core advancement wire is provided that is disposed within and extends through the lumen of the tubular braided stent body and the lumen of a distal expansion ring, and when a proximal expansion ring is provided, the core advancement wire extends through the lumen of the proximal expansion ring as well, for delivering and releasing the self-expanding stent through a delivery sheath or microcatheter to a treatment site in a patient's vasculature. The core advancement wire preferably includes a proximal portion, a distal portion, an intermediate portion located between the proximal and distal portions of the core advancement wire, and a stop member positioned between the distal portion and the intermediate portion of the core advancement wire. In a presently preferred aspect, the stop member is formed by an enlarged portion of the core advancement wire having a diameter greater than or equal to the first diameter of the compressed configuration of the expansion member. In another presently preferred aspect, the stop member is configured to engage a proximal, interior side of the distal expansion ring when the core advancement wire is advanced distally, whereby force applied distally to the core advancement wire is transmitted through the distal expansion ring to the initial deployment end or distal end of the braided stent and acts to drag and elongate the braided stent distally. The braided stent is typically configured to be delivered through the delivery sheath or microcatheter, and the core advancement wire is preferably configured to reduce friction of the braided stent with the delivery sheath or microcatheter when force is applied distally to the core advancement wire.

In another presently preferred aspect, when a proximal expansion ring is provided, the core advancement wire includes an intermediate stop member on the core advancement wire positioned on the intermediate portion of the core advancement wire within the lumen of the braided stent distal to the second expansion ring. In a presently preferred aspect, the intermediate stop member includes an enlarged portion of the core advancement wire having a diameter greater than or equal to the first diameter of the compressed configuration of the second expansion member.

In another presently preferred aspect, the present invention provides for a method of delivering and releasing the self-expanding stent through a delivery sheath or microcatheter to a treatment site in a patient's vasculature, including the step of advancing the core advancement wire distally such that the distal stop member engages a proximal, interior side of the distal expansion ring, whereby force applied distally to the core advancement wire is transmitted through the distal expansion ring to the initial deployment end or distal end of the tubular self-expanding braided stent acting to drag and elongate the tubular self-expanding braided stent, reducing friction of the tubular self-expanding braided stent with the delivery sheath or microcatheter when force is applied distally to the core advancement wire. In another presently preferred aspect, the method includes the steps of dragging the distal expansion member of the tubular self-expanding braided stent distally of the delivery sheath or microcatheter while retaining the proximal expansion member of the tubular self-expanding braided stent within the delivery sheath or microcatheter, retracting the core advancement wire proximally such that the intermediate stop member engages a distal, interior side of the proximal expansion ring, retracting the initial deployment end or distal end of the tubular self-expanding braided stent within the delivery sheath or microcatheter such that the distal expansion member and the initial deployment end or distal end of the tubular self-expanding braided stent are reduced in diameter, and recapturing the tubular self-expanding braided stent within the delivery sheath or microcatheter.

These and other features and advantages of the present invention will become more apparent from the following detailed description of the preferred embodiments in conjunction with the accompanying drawings, which illustrate, by way of example, the operation of the invention.

DETAILED DESCRIPTION OF THE PREFERRED EMBODIMENTS

While stents have commonly been delivered in blood vessels such as during intravascular angioplasty treatment of occluded cardiac arteries, by use of inflatable balloons or mechanical devices that force a stent open, the weakness and tortuosity of the neurovasculature places limits on the applicability of such stents in procedures to repair neurovascular defects, and it is desirable to provide an improved self-expanding braided stent with increased its radial expansion force, particularly at the initial deployment end or distal end, that can also reduce the internal friction of the braided stent during delivery of the braided stent through a delivery sheath or microcatheter, that can be more reliably expanded and fixed at the initial deployment end or distal end of the self-expanding braided stent, and that can be recaptured following partial deployment of a distal portion of the self-expanding braided stent prior to full deployment of a later deployed portion or proximal portion of the self-expanding braided stent.

Accordingly, referring to the drawings, which are provided by way of example, and not by way of limitation, in a first embodiment, for treatment of a patient's vasculature, the present invention provides for a braided stent 10 including a tubular braided stent body 11, having a later deployed end or proximal end 12, an initial deployment end or distal end 14, and an inner lumen 16. The tubular braided stent body is preferably formed from a plurality of elongate members 18, typically formed from two or more metal wires, or polymeric fibers or strands of material, for example. In a presently preferred aspect, the braided stent is a self-expanding stent, and includes one or more expansion rings 20, each having a first end 22, a second end 24, and an inner lumen 26. The one or more expansion rings preferably are disposed within and fixedly connected to at least the initial deployment end or distal end of the tubular braided stent body, although one or more expansion rings may also be disposed within and fixedly connected to the later deployed end or proximal end of the tubular braided stent body, as will be further explained below.

Each expansion ring includes a plurality of elongated connecting arm members 30 having first ends 32 at the first end of the expansion ring, and second ends 34 at the second end of the expansion ring. The plurality of elongated connecting arm members are connected sequentially to adjacent ones of the plurality of elongated connecting arm members alternatingly at the first and second ends to form a plurality of alternating elbow connections 36 at the first and second ends of the expansion ring, so that the plurality of elongated connecting arm members of each expansion ring substantially have a zigzag configuration.

Figure 1:
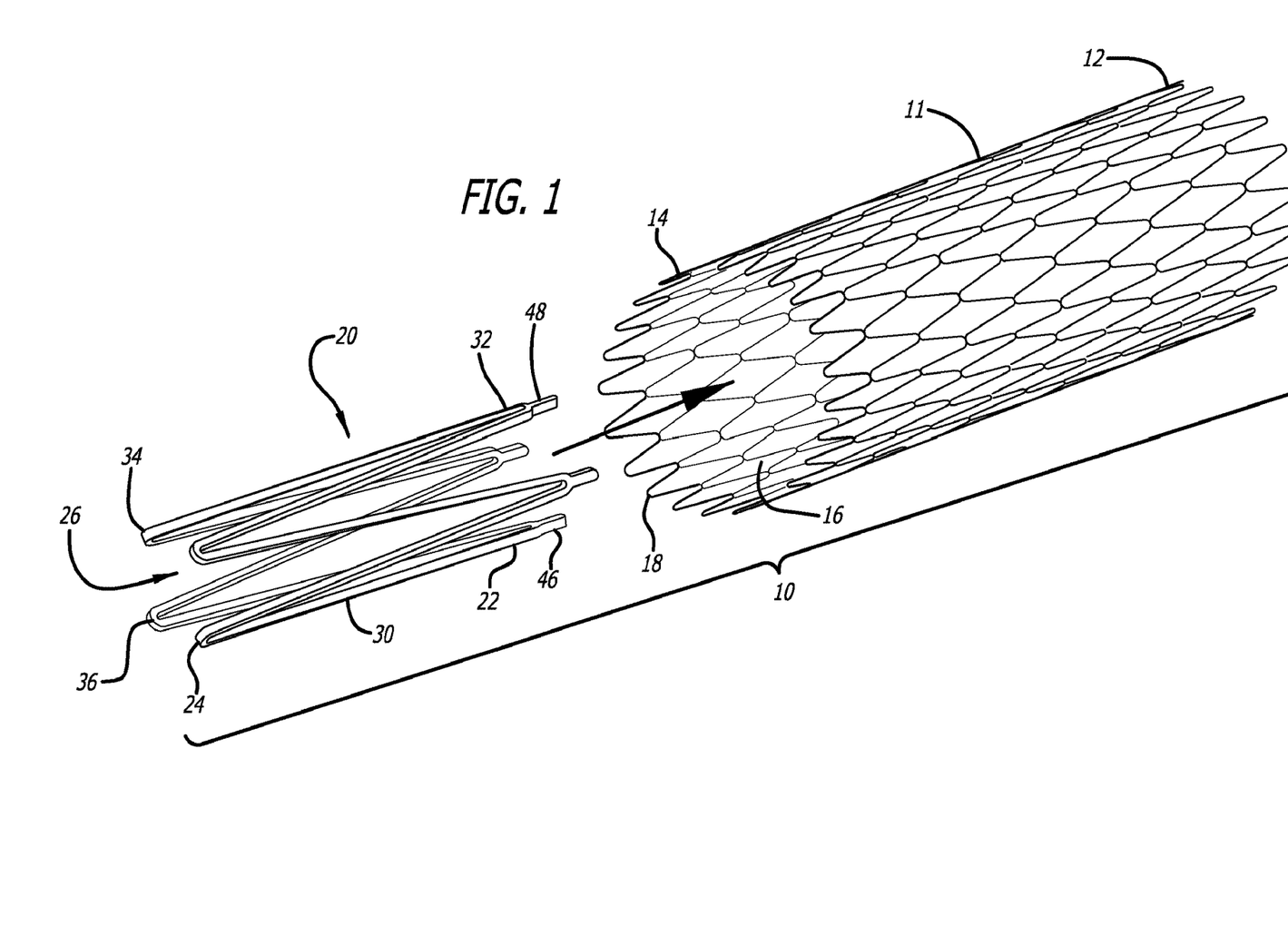
FIG. 1 is a perspective view of an expansion ring configured to be affixed within a braided stent, according to the invention.
Figure 2:
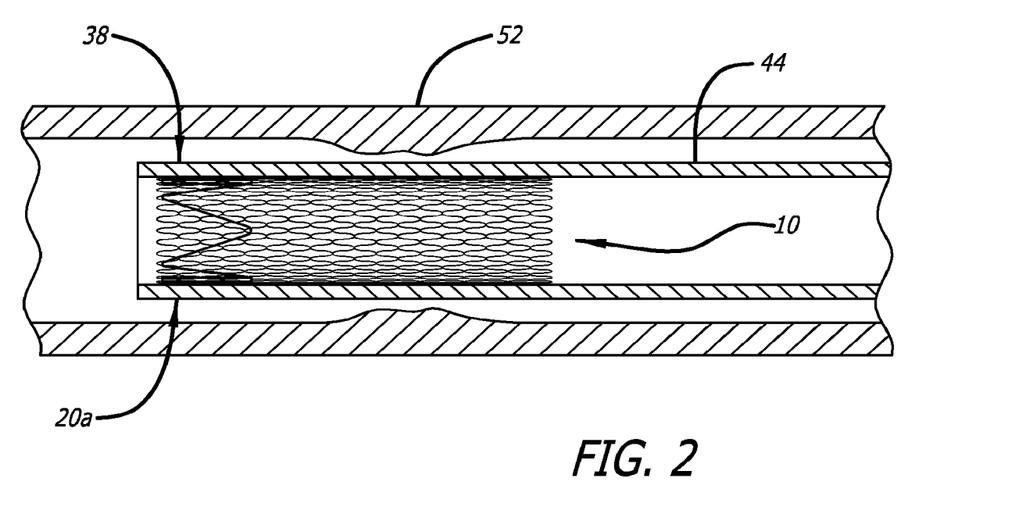
FIG. 2 is a cross-sectional schematic elevational view of an expansion ring of FIG. 1 affixed within an initial deployment end or distal end of a braided stent, shown contained within a delivery sheath or microcatheter, according to the invention.
Figure 3:
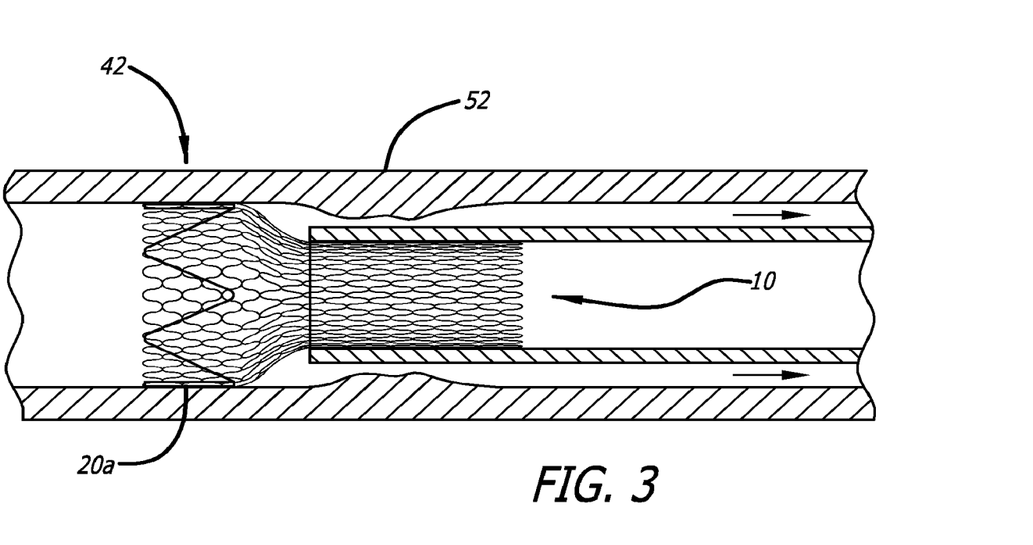
FIG. 3 is a cross-sectional schematic elevational view similar to FIG. 2, showing partial deployment of the initial deployment end or distal end of the braided stent from the delivery sheath or microcatheter of FIG. 2.
Figure 4:
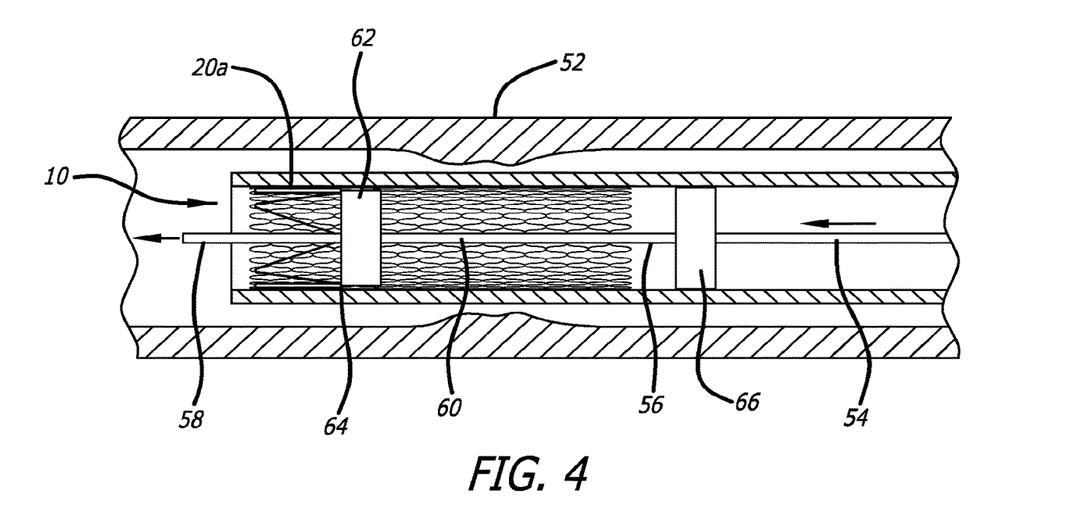
FIG. 4 is a cross-sectional schematic elevational view of an expansion ring of FIG. 1 affixed within an initial deployment end or distal end of a braided stent, shown contained within a delivery sheath or microcatheter, and including an advance wire extending through the braided stent and expansion ring, according to the invention.
Figure 5:
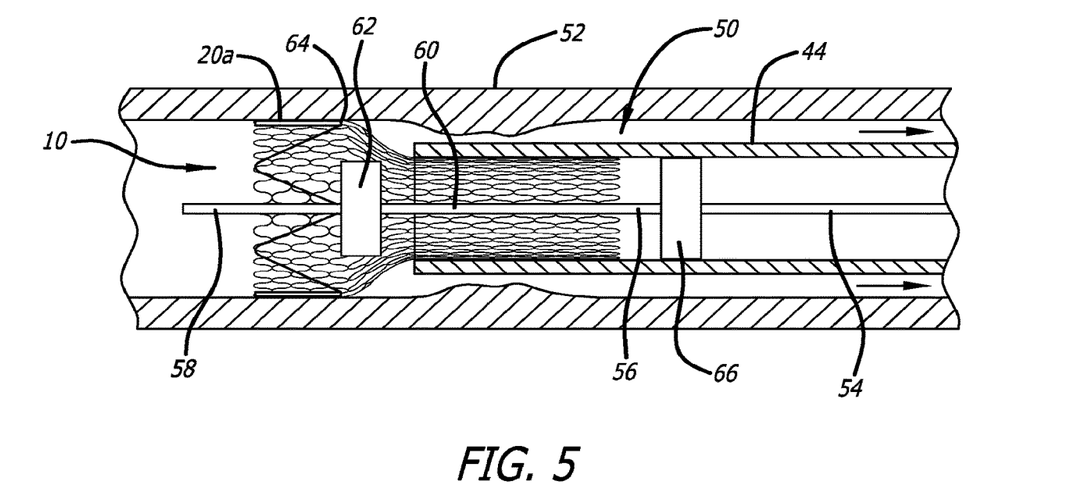
FIG. 5 is a cross-sectional schematic elevational view similar to FIG. 4, showing partial deployment of the initial deployment end or distal end of the braided stent from the delivery sheath or microcatheter of FIG. 4.
Figure 6:
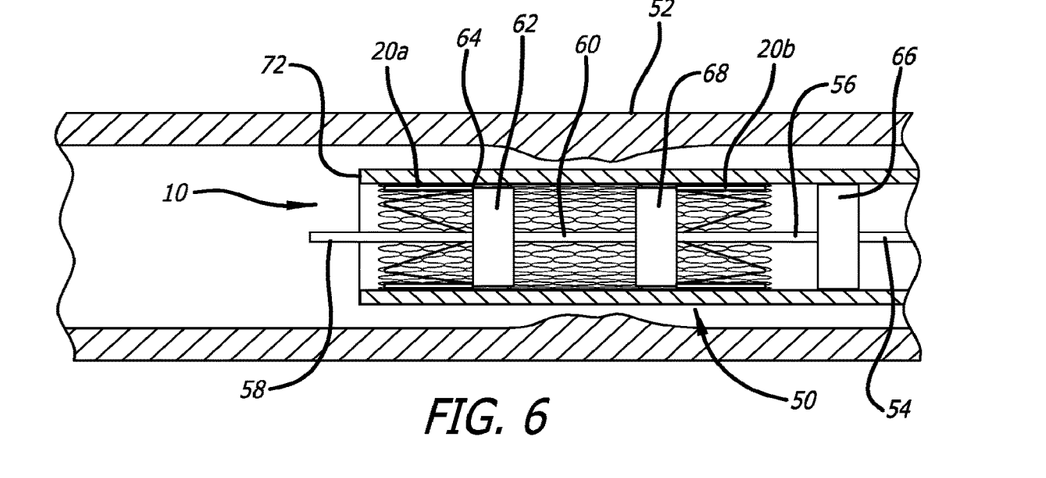
FIG. 6 is a cross-sectional schematic elevational view of a braided stent having a distal expansion ring and a proximal expansion ring affixed within the distal and proximal ends of the braided stent, shown contained within a delivery sheath or microcatheter, and including an advance wire extending through the braided stent and expansion ring, according to the invention.
Figure 7:
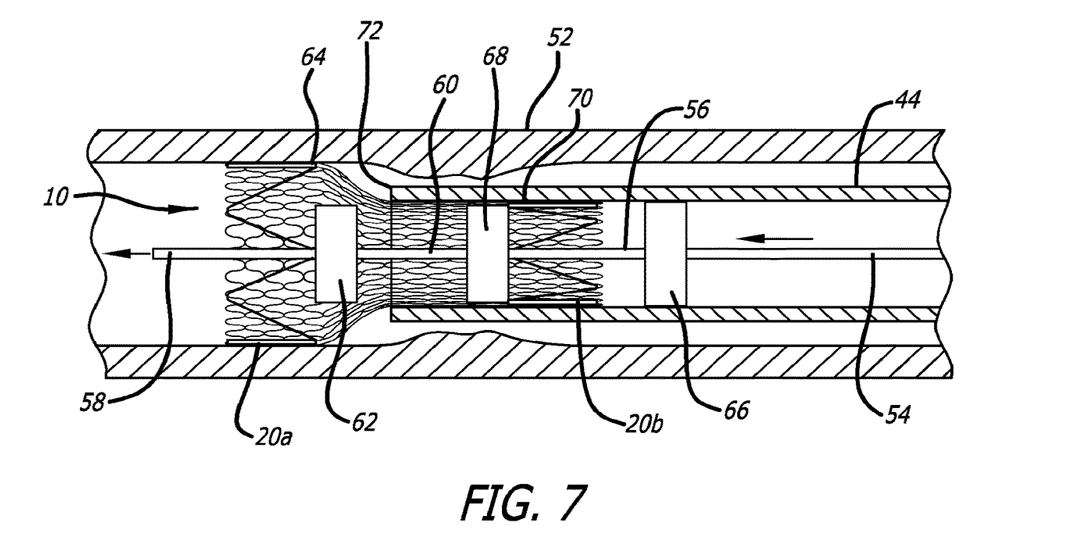
FIG. 7 is a cross-sectional schematic elevational view similar to FIG. 6, showing partial deployment of the initial deployment end or distal end of the braided stent from the delivery sheath or microcatheter of FIG. 6.

Referring to FIGS. 3 and 4, each expansion ring preferably is formed to have a compressed configuration 38, having a first diameter, and an expanded configuration 42, having a second diameter that is larger than the first diameter of the compressed configuration of the expansion ring. Each expansion ring is preferably formed of a shape memory material such as a nickel-titanium alloy, or a shape memory polymer, for example, having a shape memory position in the expanded configuration. For example, the expansion rings may be appropriately heat treated so that the expansion ring forms in the desired shape of the expanded shape memory position, with the plurality of elongated connecting arm members having a substantially zigzag type configuration. Each expansion ring is typically formed by cutting a tube formed of a shape memory material such as a nickel-titanium alloy, or a shape memory polymer, for example, by an appropriate laser. The plurality of elongated connecting arm members and the alternating elbow connections preferably can be compressed in the compressed configuration into a tubular shape that is small enough to comfortably fit within and pass through a delivery sheath or microcatheter 44 to allow delivery of the stent through the delivery sheath or microcatheter.

In another presently preferred aspect, each expansion ring includes a plurality of attachment tabs 46 connected to the plurality of alternating elbow connections at the first ends of the expansion ring. The plurality of attachment tabs preferably are connected to exterior ends 48 of the plurality of alternating elbow connections at the first ends of the one or more expansion ring. The plurality of attachment tabs preferably are fixedly connected to a tubular braided stent body, typically at or near a distal or proximal end of the tubular braided stent body, such as by welding, soldering, or gluing by an appropriate adhesive, for example. Alternatively, the attachment tabs can include holes in them so that a wire loop can be threaded through the attachment tabs, as well as through interstices of the braided stent to connect the attachment tabs and the braided stent together. In addition, two or more attachment tabs can be included at the ends of each elbow of the expansion ring, and the attachment tabs can then be used to capture a portion of the braided stent between them, after which the two or more attachment tabs can be secured together to be permanently secured to the braided stent by welding, soldering, adhesive, or the like. At least one first, distal, expansion ring 20a preferably is disposed within and fixedly connected to the initial deployment end or distal end of the tubular braided stent body. As is illustrated in FIGS. 6-9, a second, proximal, expansion ring 20b preferably also is disposed within and fixedly connected to the later deployed end or proximal end of the tubular braided stent body.

Referring to FIGS. 4-9, in a second embodiment, in which like elements are indicated by like reference numbers, the present invention further provides for an apparatus 50 for delivering and releasing a self-expanding braided stent through a delivery sheath or microcatheter to a treatment site in a patient's vasculature 52. The apparatus includes a braided stent including a tubular braided stent body, described above, and also includes a core advancement wire 54, which is disposed within and extends through the lumen of the tubular braided stent body, and is disposed within and extending through the lumen of the distal expansion ring 20a fixedly connected within the initial deployment end or distal end of the tubular braided stent body. When a proximal expansion ring 20b is fixedly connected within the later deployed end or proximal end of the tubular braided stent body, as is illustrated in FIGS. 6-9, the core advancement wire also is disposed within and extends through the lumen of the proximal expansion ring.

The core advancement wire includes a proximal portion 56, a distal portion 58, an intermediate portion 60 located between the proximal and distal portions of the core advancement wire, and a distal stop member 62 positioned between the distal portion and the intermediate portion of the core advancement wire. In one presently preferred aspect, as is shown in FIG. 4, the distal stop member is formed as an enlarged portion of the core advancement wire having a diameter greater than or equal to the first diameter of the compressed configuration of the expansion member. The distal stop member is preferably configured to engage a proximal, interior side 64 of the distal expansion ring when the core advancement wire is advanced distally, so that force applied distally to the core advancement wire is transmitted through the distal stop member to the distal expansion ring, and consequently is transmitted to the initial deployment end or distal end of the braided stent, thereby acting to drag the braided stent in a distal direction, as the braided stent is delivered through the delivery sheath or microcatheter to a treatment site, as well as to elongate the braided stent, advantageously also reducing friction with the delivery sheath or microcatheter through which the braided stent is delivered.

In another preferred aspect, a proximal stop member 66 may also be provided on the core advancement wire positioned outside and proximal to the proximal end of the braided stent. When it is provided, the proximal stop member preferably has a diameter greater than or equal to the unexpanded diameter of the compressed configuration of the braided stent and less than a diameter of the delivery sheath or microcatheter.

The self-expanding braided stent can be delivered and released through the delivery sheath or microcatheter to a treatment site in a patient's vasculature by advancing the core advancement wire distally (to the left as shown), so that the distal stop member of the core advancement wire engages the proximal, interior side of the distal expansion ring. Since the distal expansion ring is attached to the braided stent, force applied distally to the core advancement wire is transmitted through the distal expansion ring to the initial deployment end or distal end of the braided stent, and the force applied to the initial deployment end or distal end of the braided stent in the distal direction therefore tends to drag and elongate the stent, consequently reducing the diameter of the compressed configuration of the braided stent, reducing the friction between the braided stent and the delivery sheath or microcatheter.

In another embodiment illustrated in FIGS. 6-9, in which like elements are indicated by like reference numbers, the present invention further provides for an apparatus for delivering and releasing a self-expanding braided stent through a delivery sheath or microcatheter to a treatment site in a patient's vasculature, in which the core advancement wire also includes an intermediate stop member 68 positioned on the intermediate portion of the core advancement wire, within the lumen of the braided stent distal to the proximal expansion ring. The intermediate stop member preferably is formed as an enlarged portion of the core advancement wire having a diameter that is greater than or equal to the first diameter of the compressed configuration of the proximal expansion member. The intermediate stop member preferably is configured to engage the distal, interior side 70 of the proximal expansion ring when the core advancement wire is retracted proximally, allowing retraction of the braided stent within the delivery sheath or microcatheter.

Figure 8:
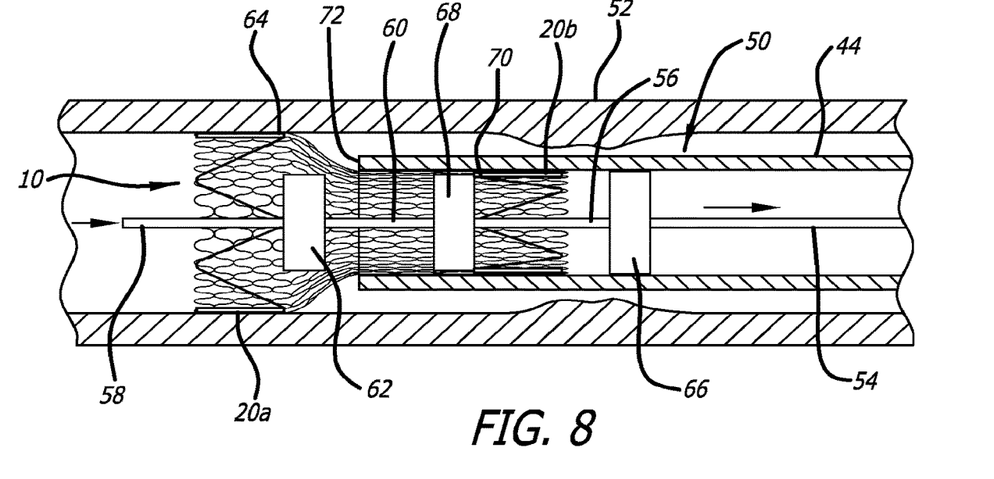
FIG. 8 is a cross-sectional schematic elevational view similar to FIG. 6, showing retraction of the initial deployment end or distal end of the braided stent into the delivery sheath or microcatheter of FIG. 6.
Figure 9:
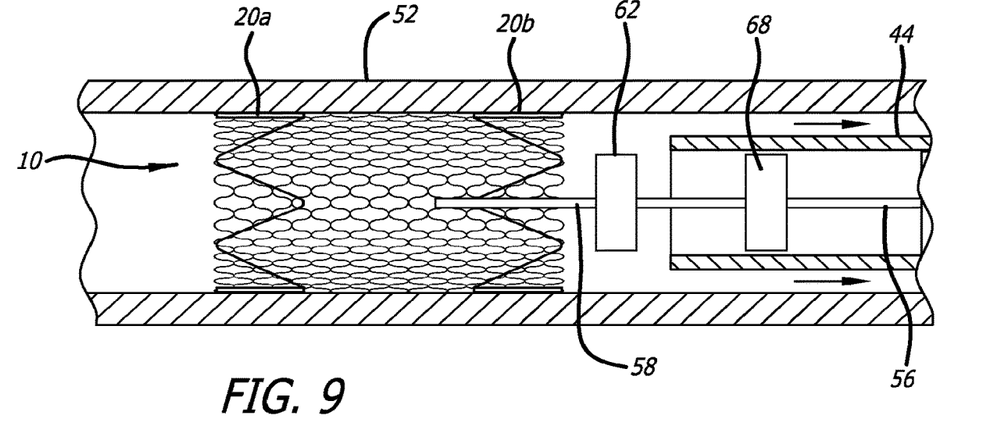
FIG. 9 is a cross-sectional schematic elevational view similar to FIG. 6, showing implantation of a braided stent at a treatment site in a patient's vasculature, and withdrawing of the advance wire and delivery sheath or microcatheter.

In this embodiment, the self-expanding braided stent can be delivered and released through the delivery sheath or microcatheter to a treatment site in a patient's vasculature by advancing the core advancement wire distally, as described above, and the core advancement wire may also then be retracted proximally (to the right as shown in FIG. 8), so that the intermediate stop member engages the distal, interior side of the proximal expansion ring. As long as the braided stent is not deployed past the proximal expansion ring, the braided stent can be recaptured in this way. The retraction force applied proximally to the delivery wire is transmitted through the proximal expansion ring to the proximal end of the braided stent, and as the braided stent is recaptured back into the delivery sheath or microcatheter, the initial deployment end or distal end of the braided stent is reduced in diameter by the mouth 72 of the sheath or microcatheter until the braided stent is again fully enclosed by the delivery sheath or microcatheter.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method of using a self-expanding braided stent in a patient's vasculature, comprising:
   delivering said self-expanding braided stent to the patient's vasculature, the stent comprising:
      a stent body having a proximal end, a distal end, and an inner lumen; and
      at least one expansion ring disposed within and fixedly connected to at least one of said proximal and distal ends,
      said at least one expansion ring having a first end, a second end, and an inner lumen,
      said at least one expansion ring having a compressed configuration having a first diameter and an expanded configuration having a second diameter larger than said first diameter;
      said at least one expansion ring comprising a distal expansion ring disposed within and fixedly connected to said distal end of said stent body,
   advancing said self-expanding braided stent distally causing said at least one expansion ring to move from said compressed configuration inside a microcatheter to said expanded configuration distal of said microcatheter;
   extending a core advancement wire within said lumen of said stent body, said core advancement wire having a proximal portion, a distal portion, an intermediate portion located between said proximal and distal portions of said core advancement wire;
   connecting said expansion ring disposed within to said distal end of said stent body;
   positioning a stop member between said distal portion and said intermediate portion of said core advancement wire; and
   applying a force distally to said core advancement wire that is transmitted through said distal expansion ring to said distal end of said braided stent thereby dragging and elongating said braided stent,
   wherein said stop member is configured to press distally into said first end of said distal expansion ring when said core advancement wire is advanced distally.

2. The method of claim 1, wherein said at least one expansion ring comprises a plurality of elongated connecting arm members having first ends at said first end of said at least one expansion ring and second ends at said second end of said expansion ring, said plurality of elongated connecting arm members being connected sequentially to adjacent ones of said plurality of elongated connecting arm members alternatingly at said first and second ends to form a plurality of alternating elbow connections at said first and second ends.

3. The method of claim 2, further comprising: forming said at least one expansion ring of shape memory material having a shape memory position in said expanded configuration.

4. The method of claim 2, further comprising: connecting a plurality of attachment tabs to said plurality of alternating elbow connections at said first ends of said at least one expansion ring.

5. The method of claim 4, wherein said plurality of alternating elbow connections at said first ends of said at least one expansion ring have exterior ends directed away from said plurality of elongated connecting arm members and said plurality of attachment tabs are connected to said exterior ends of said plurality of alternating elbow connections at said first ends of said at least one expansion ring.

6. The method of claim 4, further comprising: attaching said plurality of attachment tabs to said stent body.

7. The method of claim 1, further comprising:
   connecting a proximal expansion ring within said proximal end of said stent body; and
   spacing apart said distal expansion ring and said proximal expansion ring from each other.

8. The method of claim 1, wherein said stop member comprises an enlarged portion of said core advancement wire having a diameter greater than or equal to said first diameter of said compressed configuration of said expansion ring.

9. A method of delivering and releasing a self-expanding braided stent through a delivery sheath to a treatment site in a patient's vasculature, comprising:
   providing a tubular self-expanding braided stent body comprising an initial deployment end, an inner lumen, and an expansion ring disposed within and connected to said initial deployment end of said tubular braided stent body,
   said tubular self-expanding braided stent body comprising a compressed configuration and an expanded configuration,
   said expansion ring comprising a first end, a second end, an inner lumen, a compressed configuration having a first diameter and an expanded configuration having a second diameter larger than said first diameter,
   said expansion ring further comprising a distal expansion ring disposed within and fixedly connected to said distal end of said stent body, and
   a core advancement wire disposed within and extending through said lumen of said tubular braided stent body and said lumen of said expansion ring, said core advancement wire having a proximal portion, a distal portion, an intermediate portion located between said proximal and distal portions of said core advancement wire, and
   a distal stop member positioned between said distal portion and said intermediate portion of said core advancement wire; and
   advancing said core advancement wire longitudinally such that said distal stop member presses distally into said first end of said distal expansion ring, whereby force applied longitudinally to said core advancement wire is transmitted through said distal expansion ring to said initial deployment end of said tubular self-expanding braided stent body acting to drag and elongate said tubular self-expanding braided stent body.

10. The method of claim 9, further comprising: reducing friction of said tubular self-expanding braided stent body with said delivery sheath by applying a force longitudinally to said core advancement wire.

11. The method of claim 9, wherein said expansion ring comprises:
   a plurality of elongated connecting arm members having first ends at said first end of said expansion ring and second ends at said second end of said expansion ring, said plurality of elongated connecting arm members being connected sequentially to adjacent ones of said plurality of elongated connecting arm members alternatingly at said first and second ends to form a plurality of alternating elbow connections at said first and second ends.

12. The method of claim 11, further comprising: forming said at least one expansion ring of shape memory material having a shape memory position in said expanded configuration.

13. The method of claim 11, further comprising: connecting a plurality of attachment tabs to said plurality of alternating elbow connections at said first ends of said expansion ring.

14. The method of claim 13, wherein said plurality of alternating elbow connections at said first ends of said expansion ring have exterior ends directed away from said plurality of elongated connecting arm members and said plurality of attachment tabs are connected to said exterior ends of said plurality of alternating elbow connections at said first ends of said expansion ring.

15. The method of claim 13, the method further comprising:
connecting a proximal expansion ring within said proximal end of said tubular braided stent body; and
spacing apart said distal expansion ring and said proximal expansion ring from each other.

16. The method of claim 9, further comprising: attaching said plurality of attachment tabs to said tubular braided stent body.

17. A method of delivering and releasing a self-expanding braided stent through a delivery sheath to a treatment site in a patient's vasculature, comprising:
positioning a tubular self-expanding braided stent body in the patient's vasculature, the tubular self-expanding braided stent body having a compressed configuration and an expanded configuration, comprising:
a proximal end,
a distal end,
an inner lumen,
a distal expansion ring having a proximal end, a distal end, and an inner lumen, said distal expansion ring disposed within and fixedly connected to said distal end of said tubular self-expanding braided stent body, and
a proximal expansion ring having a proximal end, a distal end, and an inner lumen, said proximal expansion ring disposed within and fixedly connected to said proximal end of said tubular self-expanding braided stent body,
wherein each of said distal and proximal expansion rings comprising:
a compressed configuration having a first diameter; and
an expanded configuration having a second diameter larger than said first diameter; and
a core advancement wire disposed within and extending through said lumen of said tubular braided stent body, said lumen of said distal expansion ring, and said lumen of said proximal expansion ring, said core advancement wire having a proximal portion, a distal portion, an intermediate portion located between said proximal and distal portions of said core advancement wire,
a distal stop member positioned between said distal portion and said intermediate portion of said core advancement wire and an intermediate stop member on said core advancement wire positioned on said intermediate portion of said core advancement wire within said lumen of said tubular self-expanding braided stent body distal to said proximal expansion ring;
advancing said core advancement wire distally such that said distal stop member presses distally into said first end of said distal expansion ring, whereby force applied distally to said core advancement wire is transmitted through said distal expansion ring to said distal end of said tubular self-expanding braided stent body to drag and elongate said tubular self-expanding braided stent body;
dragging said distal expansion ring of said tubular self-expanding braided stent body distally of said delivery sheath while retaining said proximal expansion ring of said tubular self-expanding braided stent body within said delivery sheath;
retracting said core advancement wire proximally such that said intermediate stop member presses proximally into said first end of said proximal expansion ring; and
retracting said distal end of said tubular self-expanding braided stent body within said delivery sheath such that said distal expansion ring and said distal end of said tubular self-expanding braided stent body are reduced in diameter; and
recapturing said tubular self-expanding braided stent body within said delivery sheath.

* * * * *